United States Patent
Kondo et al.

(10) Patent No.: US 10,668,125 B2
(45) Date of Patent: Jun. 2, 2020

(54) PEPTIDE HAVING HIGHLY-SHIFTED ACCUMULATION TO PANCREATIC CANCER CELLS AND TISSUES, AND USE OF SAID PEPTIDE

(71) Applicant: Niigata University, Niigata-shi, Niigata (JP)

(72) Inventors: Eisaku Kondo, Niigata (JP); Ken Saito, Niigata (JP)

(73) Assignee: Niigata University, Niigata-shi (JP)

( * ) Notice: Subject to any disclaimer, the term of this patent is extended or adjusted under 35 U.S.C. 154(b) by 0 days.

(21) Appl. No.: 15/776,609

(22) PCT Filed: Oct. 21, 2016

(86) PCT No.: PCT/JP2016/081287
§ 371 (c)(1),
(2) Date: May 16, 2018

(87) PCT Pub. No.: WO2017/086090
PCT Pub. Date: May 26, 2017

(65) Prior Publication Data
US 2018/0360903 A1    Dec. 20, 2018

(30) Foreign Application Priority Data

Nov. 19, 2015 (JP) ................................ 2015-226228

(51) Int. Cl.
| | | |
|---|---|---|
| *A61K 38/02* | (2006.01) | |
| *A61K 45/06* | (2006.01) | |
| *A61K 47/36* | (2006.01) | |
| *A61K 47/42* | (2017.01) | |
| *A61P 35/00* | (2006.01) | |
| *C07K 7/06* | (2006.01) | |
| *C07K 7/08* | (2006.01) | |
| *C12N 15/62* | (2006.01) | |
| *A61K 38/01* | (2006.01) | |
| *G01N 33/574* | (2006.01) | |
| *A61K 49/00* | (2006.01) | |
| *A61K 9/00* | (2006.01) | |

(52) U.S. Cl.
CPC ............ *A61K 38/012* (2013.01); *A61K 38/02* (2013.01); *A61K 45/06* (2013.01); *A61K 47/36* (2013.01); *A61K 47/42* (2013.01); *A61K 49/0043* (2013.01); *A61K 49/0056* (2013.01); *A61P 35/00* (2018.01); *C07K 7/06* (2013.01); *C07K 7/08* (2013.01); *C12N 15/62* (2013.01); *G01N 33/57438* (2013.01); *A61K 9/0019* (2013.01)

(58) Field of Classification Search
CPC ...... A61K 38/012; A61K 38/02; A61K 45/06; A61K 47/36; A61K 47/42; A61K 49/0043; A61K 49/0056; A61K 9/0019; A61P 35/00; C07K 7/06; C07K 7/08; C12N 15/62; G01N 33/57438
USPC ........ 530/300, 328, 327; 514/1.1, 21.6, 21.5
See application file for complete search history.

(56) References Cited

U.S. PATENT DOCUMENTS

| | | | |
|---|---|---|---|
| 6,703,491 B1 * | 3/2004 | Homburger | ........ A01K 67/0333 435/252.3 |
| 2006/0270005 A1 * | 11/2006 | Marliere | .............. C07D 473/16 435/91.2 |
| 2008/0020978 A1 * | 1/2008 | Gegg, Jr. | ............. A61K 38/225 424/1.69 |
| 2008/0193510 A1 | 8/2008 | Wu et al. | |
| 2010/0048487 A1 | 2/2010 | Uno et al. | |
| 2010/0137187 A1 | 6/2010 | Barton et al. | |
| 2017/0039314 A1 * | 2/2017 | Bremel | ................ A61K 39/085 |

FOREIGN PATENT DOCUMENTS

| | | |
|---|---|---|
| JP | 2010-259371 A | 11/2010 |
| JP | 5043672 B2 | 7/2012 |
| JP | 5721140 B | 4/2015 |
| WO | 2009/129220 A2 | 10/2009 |

OTHER PUBLICATIONS

Verhoef et al., "Questioning the Use of PEGylation for Drug Delivery," Drug. Deliv. Transl. Res., 3(6): 499-503. (Year: 2013).*
International Search Report dated Jan. 24, 2017, issued in corresponding International Application No. PCT/JP2016/081287, filed Oct. 21, 2016, 3 pages.
Vivès, E., et al., "A Truncated HIV-1 Tat Protein Basic Domain Rapidly Translocates Through the Plasma Membrane and Accumulates in the Cell Nucleus," Journal of Biological Chemistry 272(25):16010-16017, Jun. 1997.
Extended European Search Report dated Mar. 19, 2019, issued in corresponding European Application No. 16866092.6, filed Oct. 21, 2016, 9 pages.
Lewis, H.D., et al., "Creation of a Novel Peptide With Enhanced Nuclear Localization in Prostate and Pancreatic Cancer Cell Lines," BMC Biotechnology 10(1):79, Oct. 2010, 12 pages.
Zheng, Y., et al, "FITC-Conjugated Cyclic RGD Peptides as Fluorescent Probes for Staining Integrin αvβ3/αvβ5 in Tumor Tissues," Bioconjugate Chemistry 25(11):1925-1941, Oct. 2014.

* cited by examiner

*Primary Examiner* — Julie Ha
(74) *Attorney, Agent, or Firm* — Christensen O'Connor Johnson Kindness PLLC

(57) ABSTRACT

Disclosed is a peptide of the following (a) or (b): (a) a peptide containing an amino acid sequence including a sequence set forth in any one of SEQ ID NOS: 1, 2, 3, and 4; and (b) a peptide containing an amino acid sequence including a sequence having at least 60% identity with a sequence set forth in any one of SEQ ID NOS: 1, 2, 3, and 4, the peptide having highly-shifted accumulation to pancreatic cancer cells and tissues.

6 Claims, 6 Drawing Sheets

Specification includes a Sequence Listing.

SEQUENCE LISTING

<160> NUMBER OF SEQ ID NOS: 13

<210> SEQ ID NO 1
<211> LENGTH: 15
<212> TYPE: PRT
<213> ORGANISM: Artificial Sequence
<220> FEATURE:
<223> OTHER INFORMATION: Synthesized

<400> SEQUENCE: 1

Gly Tyr Arg Arg Thr Thr Pro Ser Tyr Trp Arg Met Trp Leu Arg
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Synthesized

<400> SEQUENCE: 2

Ala Arg Arg Tyr Thr Trp Ile Arg Ala
1               5

<210> SEQ ID NO 3
<211> LENGTH: 9
<212> TYPE: PRT
<213> ORGANISM: Artificial Sequence
<220> FEATURE:
<223> OTHER INFORMATION: Synthesized

<400> SEQUENCE: 3

Arg Ala Trp Arg Gln Cys Arg Trp Arg
1               5

<210> SEQ ID NO 4
<211> LENGTH: 9
<212> TYPE: PRT
<213> ORGANISM: Artificial Sequence
<220> FEATURE:
<223> OTHER INFORMATION: Synthesized

<400> SEQUENCE: 4

Arg Arg Pro Thr Thr Trp His Lys Pro
1               5

<210> SEQ ID NO 5
<211> LENGTH: 17
<212> TYPE: PRT
<213> ORGANISM: Artificial Sequence
<220> FEATURE:
<223> OTHER INFORMATION: Synthesized

<400> SEQUENCE: 5

Cys Gly Tyr Arg Arg Thr Thr Pro Ser Tyr Trp Arg Met Trp Leu Arg
1               5                   10                  15

Cys

<210> SEQ ID NO 6
<211> LENGTH: 11
<212> TYPE: PRT
<213> ORGANISM: Artificial Sequence
<220> FEATURE:
<223> OTHER INFORMATION: Synthesized

<400> SEQUENCE: 6

Cys Ala Arg Arg Tyr Thr Trp Ile Arg Ala Cys
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthesized

<400> SEQUENCE: 7

Cys Arg Ala Trp Arg Gln Cys Arg Trp Arg Cys
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthesized

<400> SEQUENCE: 8

Cys Arg Arg Pro Thr Thr Trp His Lys Pro Cys
1               5                   10

<210> SEQ ID NO 9
<211> LENGTH: 45
<212> TYPE: DNA
<213> ORGANISM: Artificial Sequence
<220> FEATURE:
<223> OTHER INFORMATION: Synthesized

<400> SEQUENCE: 9
ggatatcggc ggaccacccc ttcctactgg cgcatgtggc tgcgg            45

<210> SEQ ID NO 10
<211> LENGTH: 27
<212> TYPE: DNA
<213> ORGANISM: Artificial Sequence
<220> FEATURE:
<223> OTHER INFORMATION: Synthesized

<400> SEQUENCE: 10
gcgcggcggt atacgtggat tcgggct            27

<210> SEQ ID NO 11
<211> LENGTH: 27
<212> TYPE: DNA
<213> ORGANISM: Artificial Sequence
<220> FEATURE:
<223> OTHER INFORMATION: Synthesized

<400> SEQUENCE: 11
cgtgcgtggc ggcagtgtcg gtggcgt            27

<210> SEQ ID NO 12
<211> LENGTH: 27
<212> TYPE: DNA
<213> ORGANISM: Artificial Sequence
<220> FEATURE:
<223> OTHER INFORMATION: Synthesized

<400> SEQUENCE: 12
cggcggccga ctacgtggca taagcct            27

<210> SEQ ID NO 13

```
<211> LENGTH: 9
<212> TYPE: PRT
<213> ORGANISM: Artificial Sequence
<220> FEATURE:
<223> OTHER INFORMATION: Synthesized

<400> SEQUENCE: 13

Arg Arg Arg Arg Arg Arg Arg Arg Arg
1               5
```

PEPTIDE HAVING HIGHLY-SHIFTED ACCUMULATION TO PANCREATIC CANCER CELLS AND TISSUES, AND USE OF SAID PEPTIDE

TECHNICAL FIELD

The present invention relates to a peptide having highly-shifted accumulation to pancreatic cancer cells and tissues, and use of the peptide.

Priority is claimed on Japanese Patent Application No. 2015-226228, filed on Nov. 19, 2015, the content of which is incorporated herein by reference.

BACKGROUND ART

Pancreatic cancer (particularly, invasive pancreatic duct cancer) shows a mean survival time of approximately 6 months after diagnosis and is known to be intractable among malignant tumors. According to the vital statistics of population published by the Ministry of Health, Labour and Welfare of Japan, the annual number of deaths caused by pancreatic malignant tumors increases every year, and the number reached 26,791 according to the statistics of the year 2009. Furthermore, the proportion of deaths caused by pancreatic cancer occupied 9% of all cancer fatalities, and pancreatic cancer ranks the fifth after lung cancer, stomach cancer, colon cancer, and liver cancer.

According to the National Pancreatic Cancer Registration Investigation Report (year 1999), cases of resectable pancreatic cancer occupied 39% of all cases. Furthermore, the five-year survival rate is as low as 13%.

Regarding the reason why treatment of pancreatic cancer is difficult, one of the reasons may be that since there are only few subjective symptoms in the state of early stage, an early discovery is very difficult. In many cases, as cancer develops, symptoms such as abdominal pain, body weight reduction, and jaundice appear, and thereby cancer is discovered. Therefore, in a majority of cases, at the time of discovery by the manifestation of noticeable symptoms, the cancer is already in a state of advanced cancer without any surgical indications or limited to palliative operations.

Another reason why treatment is difficult may be that pancreatic cancer has characteristics of easily invading or metastasizing from the early stage. Another reason may be that since the pancreas is located at a retroperitoneal site and is positioned on the dorsal side of many intra-abdominal organs, during radiation therapy, it is difficult to irradiate only the diseased site of the pancreas with radiation. Therefore, radiation therapy has a high possibility of causing serious adverse side effects and may be excluded from applicable treatment options.

Currently, examples of the method for investigation or diagnosis of pancreatic cancer include examination methods such as biochemical examination of blood, abdominal ultrasonography, Endoscopic retrograde cholangiopancreatography (ERCP) examination, Computed Tomography (CT) combined with the use of a contrast agent, Magnetic resonance imaging (MRI), and a Positron Emission Tomography (PET) method (particularly, fluorodeoxy glucose (FDG)-PET method).

Meanwhile, in regard to the trend of utilizing peptides as biomaterials in the field of medicine, attention has been paid to cell membrane-permeable (cell-absorbable) peptides such as Tat, penetratin, and polyarginine.

However, since these peptides are generally and non-selectively absorbed without distinction between normal cells or normal tissues and tumor cells or tumor tissues, applying these peptides to therapeutic drug delivery system (DDS) tools for malignant tumors, where target-selective drug delivery is required, is not readily utilizable from the viewpoint of inducing serious adverse side effects. Particularly, cell membrane-permeable (cell-absorbable) peptides such as Tat, which are globally used in experimental systems, are known to have a property of accumulating in the liver (see, for example, Non-Patent Document 1).

In contrast, cyclic RGD is the only peptide that has been acknowledged as a medicine. Cyclic RGD is targeted at $\alpha_v\beta_3$ integrin, which has been reported to be expressed at a high level in the vascular endothelial cells that constitute new blood vessels or existing blood vessels (and some tumor cells) and has a point of action in vascular permeability enhancement. Therefore, cyclic RGD is applied as an imaging agent or a DDS preparation, not alone but in the form of simultaneous combined use with other drugs (see, for example, Patent Document 1).

CITATION LIST

Patent Literature

[Patent Document 1] Japanese Patent No. 5721140

Non-Patent Literature

[Non-Patent Document 1] Vives E., et al., A truncated HIV-1 Tat Protein Basic Domain Rapidly Translocates through the Plasma Membrane and Accumulates in the Cell Nucleus, J. Biol. Chem., 272, 16010-16017, 1997.

SUMMARY OF INVENTION

Technical Problem

Pancreatic cancer is very well recognized as one of the most unfavorable tumors among polyphyletic malignant tumors, for which curative treatment is still difficult even at present in the field of cancer medicine, and there is a demand for an effective therapeutic method that is directly linked to an improvement of survival rate.

In the methods for examination and diagnosis of pancreatic cancer described above, the determination criterion of the examination results is abnormal shadow judgment. In the shadow judgment, there are limitations in view of accuracy, including spread of the lesion.

Furthermore, since cyclic RGD described in Patent Document 1 is not a peptide that is targeted at tumor cells and tumor tissues themselves, cyclic RGD is a novel material from the viewpoint of being a peptide having a performance of directly capturing cancer, and there is still room for improvement in view of anticancer medical technology requiring efficient cancer control.

The present invention was achieved in view of such circumstances as described above, and it is an object of the invention to provide a novel peptide that acts directly on pancreatic cancer cells and tissues and has highly-shifted accumulation thereto.

Solution to Problem

That is, the present invention includes the following embodiments.

[1] A peptide of the following (a) or (b):
(a) a peptide containing an amino acid sequence including a sequence set forth in any one of SEQ ID NOS: 2, 3, and 4; and
(b) a peptide containing an amino acid sequence including a sequence having at least 70% identity with a sequence set forth in any one of SEQ ID NOS: 2, 3, and 4, the peptide having highly-shifted accumulation to pancreatic cancer cells and tissues.

[2] The peptide according to [1], which is a peptide including L-amino acids.

[3] A nucleic acid encoding the peptide according to [1] or [2].

[4] A vector including the nucleic acid according to [3].

[5] A carrier including the peptide according to [1] or [2].

[6] The carrier according to [5], further including one of the group consisting of a marker and a modifier.

[7] The carrier according to [6], in which the marker is one of the group consisting of a stable isotope, a radioisotope, and a fluorescent substance.

[8] The carrier according to [6] or [7], in which the modifier is one of the group consisting of a sugar chain and polyethylene glycol.

[9] A pharmaceutical composition including:
the carrier according to any one of [5] to [8]; and
a physiologically active substance.

[10] The pharmaceutical composition according to [9], which is used for treatment or diagnosis of pancreatic cancer.

Advantageous Effects of Invention

According to the invention, a novel peptide having highly-shifted accumulation to pancreatic cancer cells and tissues can be provided.

Furthermore, pancreatic cancer lesions including metastatic lesions can be detected in vivo conveniently and selectively with high sensitivity.

DESCRIPTION OF EMBODIMENTS

Figure 1:
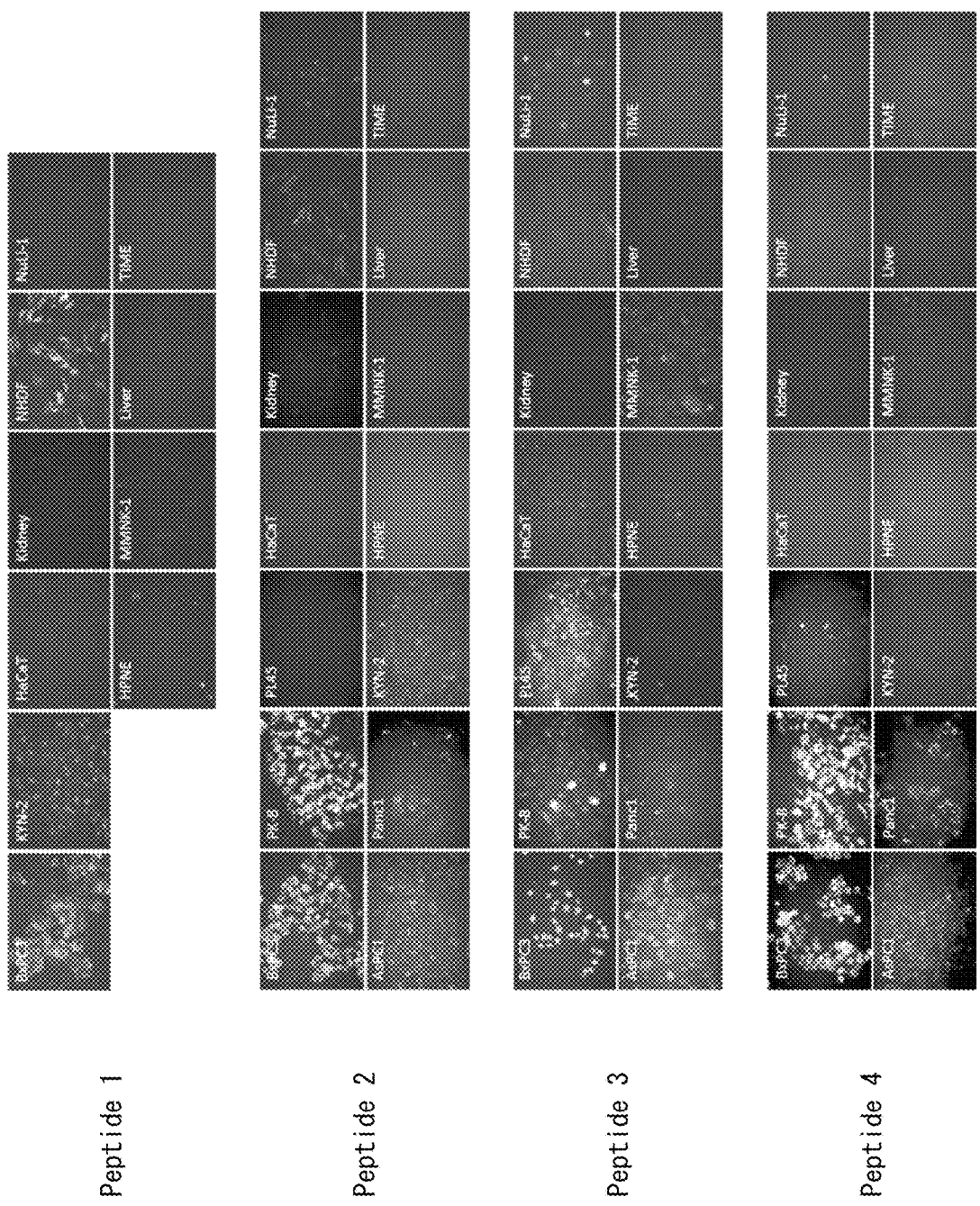
FIG. 1 is a set of fluorescence microscopic photographs of various pancreatic cancer cells, other cancer cells, and normal cells derived from various tissues, to which various peptides were added in Test Example 1.

[Peptide Having Highly-Shifted Accumulation to Pancreatic Cancer Cells and Tissues]

According to an embodiment, the invention provides a peptide of the following (a) or (b):
(a) a peptide containing an amino acid sequence including a sequence set forth in any one of SEQ ID NOS:1, 2, 3, and 4; and
(b) a peptide containing an amino acid sequence having at least 60% identity with a sequence set forth in any one of SEQ ID NOS:1, 2, 3, and 4, the peptide having highly-shifted accumulation to pancreatic cancer cells and tissues.

The peptide of the present embodiment is a novel peptide having highly-shifted accumulation to pancreatic cancer cells and tissues.

The inventors of the present invention found a novel peptide having highly-shifted accumulation to pancreatic cancer cells and tissues, by an in vitro virus (IVV) method, and thus the inventors completed the invention.

In the IVV method, puromycin, which is a kind of antibiotic substance, is conjugated to the 3'-terminal of mRNA via a PEG (polyethylene glycol) spacer, and a cell-free translation reaction is carried out by using the conjugate as a template. Thereby, a simple mRNA-protein bonded molecule IVV, in which a protein is covalently bonded to a mRNA via puromycin, is established. The inventors of the invention established an IVV library by autonomously producing IVV's. From this IVV library thus established, an IVV including a protein that binds to a bait (lure) is pulled in in vitro, subsequently the mRNA linked thereto is subjected to reverse transcription and amplified by PCR, and the base sequence is decoded. Thereby, a group of interacting proteins can be identified using a very small amount (sensitivity of 1,000 times or higher compared to the mass analysis method).

The peptide of the present embodiment includes a peptide of the following (a).
(a) A peptide containing an amino acid sequence including a sequence set forth in any one of SEQ ID NOS:1, 2, 3, and 4.

The amino acid sequences set forth in SEQ ID NOS:1, 2, 3, and 4 with regard to (a) are sequences represented by the following amino acid sequences.

GYRRTTPSYWRMWLR (SEQ ID NO: 1)

ARRYTWIRA (SEQ ID NO: 2)

RAWRQCRWR (SEQ ID NO: 3)

RRPTTWHKP (SEQ ID NO: 4)

The peptide of (a) has highly-shifted accumulation to pancreatic cancer cells and tissues. The peptide of the present embodiment has highly-shifted accumulation to pancreatic cancer cells and tissues, even if the peptide is a peptide containing only an amino acid sequence set forth in SEQ ID NOS:1, 2, 3, and 4.

According to the present specification, "pancreatic cancer" means a tumor occurred in the pancreas and is also referred to as pancreas cancer.

The pancreas includes acini that produce the pancreatic juice; ducts that transfer the pancreatic juice; and islets of Langerhans, which are endocrine glands. Cancer can occur in any of those tissues; however, cancer develops into tumors that respectively exhibit completely different characteristics. Examples of the type of pancreatic cancer include invasive pancreatic duct cancer, pancreatic endocrine tumor, intraductal papillary mucinous tumor, mucinous cystic tumor, acinic cell carcinoma, serous cystadenocarcinoma, and metastatic pancreatic cancer. Among them, invasive pancreatic duct cancer occupies 80% to 90% of neoplastic lesions occurring in the pancreas.

Since the peptide of (a) as described above has highly-shifted accumulation to all kinds of pancreatic cancers mentioned above, as will be described below, all kinds of pancreatic cancers can be selectively detected with high sensitivity by using the peptide of (a) as a carrier. Furthermore, all kinds of pancreatic cancers can be treated. Above all, it is preferable to apply the peptide of (a) to the invasive pancreatic duct cancer, which is a representative neoplastic lesion occurring in the pancreas.

According to the present specification, the term "highly-shifted accumulation to pancreatic cancer cells and tissues" means properties of being absorbed to a high degree into pancreatic cancer cells compared to normal tissues in vivo and tumor cells of other strains.

The peptide of the present embodiment includes a peptide of the following (b) as a peptide that is functionally equivalent to the peptide of (a) described above.

(b) A peptide containing an amino acid sequence having at least 60% identity with an amino acid sequence set forth in any one of SEQ ID NOS:1, 2, 3, and 4, the peptide having highly-shifted accumulation to pancreatic cancer cells and tissues.

Since this peptide is functionally equivalent to the peptide of (a) described above, the peptide has an identity of at least 60% with the peptide of (a). Such identity is preferably at least 70%, more preferably at least 80%, even more preferably at least 85%, particularly preferably at least 90%, and most preferably at least 95%.

Furthermore, the peptide of (b) has highly-shifted accumulation to pancreatic cancer cells and tissues.

Here, the sequence identity of an object amino acid sequence with respect to the reference amino acid sequence can be determined, for example, as follows. First, the reference amino acid sequence and the object amino acid sequence are aligned. Here, the respective amino acid sequences may include gaps so that the sequence identity is maximized. Subsequently, the number of coincident amino acids is calculated for the reference amino acid sequence and the object amino acid sequence, and the sequence identity can be determined according to the following Formula (1).

"Sequence identity (%)"=[Number of coincident amino acids]/[total number of amino acids of object amino acid sequence]×100         (1)

The peptide of (a) or (b) may also have a cyclic structure. By having a cyclic structure, the peptide can be easily absorbed only into pancreatic cancer cells. The peptide of (a) or (b) may be composed of L-amino acids, D-amino acids, or a combination of these, and it is preferable that the peptide is a peptide composed of L-amino acids.

L-amino acids are naturally occurring amino acids, and D-amino acids are amino acids having reverse chirality of L-amino acid residues. Furthermore, in order to enhance the highly-shifted accumulation to pancreatic cancer cells and tissues, or in order to optimize other physical properties, the peptide may be chemically modified.

It is preferable that the peptide of (a) or (b) further includes a cysteine residue at the N-terminal and the C-terminal. Specifically, an amino acid sequence set forth in the following SEQ ID NO:3 may be mentioned.

CGYRRTTPSYWRMWLRC (SEQ ID NO: 5)

CARRYTWIRAC (SEQ ID NO: 6)

CRAWRQCRWRC (SEQ ID NO: 7)

CRRPTTWHKPC (SEQ ID NO: 8)

By including a cysteine residue at the N-terminal and the C-terminal, the peptide of the present embodiment can adopt a cyclized form by utilizing a disulfide bond between the thiol groups carried by the cysteine residues.

[Nucleic Acid Encoding Peptide]

According to an embodiment, the invention provides a nucleic acid that encodes the above-mentioned peptide.

When the nucleic acid of the present embodiment is used, a peptide having highly-shifted accumulation to pancreatic cancer cells and tissues can be obtained.

Examples of the nucleic acid encoding the peptide described above include a nucleic acid containing a base sequence set forth in any one of SEQ ID NOS:9, 10, 11, and 12; and a nucleic acid containing a base sequence having at least 80%, for example, at least 85%, for example, at least 90%, or for example, at least 95%, identity with a base sequence set forth in any one of SEQ ID NOS:9, 10, 11, and 12, the base sequence being any combination of base sequences encoding the various amino acids that serve as constituent components of a peptide having highly-shifted accumulation to pancreatic cancer cells and tissues. The base sequence set forth in SEQ ID NO:9 is a base sequence of a nucleic acid that encodes a peptide containing the amino acid sequence set forth in SEQ ID NO:1 described above, and the base sequence set forth in SEQ ID NO:10 is a base sequence of a nucleic acid that encodes a peptide containing the amino acid sequence set forth in SEQ ID NO:2. The base sequence set forth in SEQ ID NO:11 is a base sequence of a nucleic acid that encodes a peptide containing the amino acid sequence set forth in SEQ ID NO:3, and the base sequence set forth in SEQ ID NO:12 is a base sequence of a nucleic acid that encodes a peptide containing the amino acid sequence set forth in SEQ ID NO:4.

Here, the sequence identity of an object base sequence with respect to the reference base sequence can be determined, for example, as follows. First, the reference base sequence and an object base sequence are aligned. Here, the respective base sequences may include gaps so that the sequence identity is maximized. Subsequently, the base number of coincident bases is calculated for the reference base sequence and the object base sequence, and the sequence identity can be determined according to the following Formula (2).

"Sequence identity (%)"=[Number of coincident bases]/[total number of bases of object base sequence]×100   (2)

[Vector Including Nucleic Acid That Encodes Peptide]

According to an embodiment, the invention provides a vector including the nucleic acid described above.

When the vector of the present embodiment is used, a peptide having highly-shifted accumulation to pancreatic cancer cells and tissues can be obtained.

The vector of the present embodiment is preferably an expression vector. The expression vector is not particularly limited, and for example, *Escherichia coli*-derived plasmids such as pBR322, pBR325, pUC12, and pUC13; Bacillus subtilis-derived plasmids such as pUB110, pTP5, and pC194; yeast-derived plasmids such as pSH19 and pSH15; bacteriophages such as λ phage; viruses such as adenovirus, adeno-associated virus, lentivirus, vaccinia virus, baculovirus, retrovirus, and hepatitis virus; and vectors obtained by modifying these, can be used.

In regard to the expression vectors mentioned above, there are no particular limitations on the promoter for expressing the peptide mentioned above, and for example, promoters for expression using animal cells as hosts, such as EF1α promoter, SRa promoter, SV40 promoter, LTR promoter, cytomegalovirus (CMV) promoter, and HSV-tk promoter; promoters for expression using plant cells as hosts, such as 35S promoter of cauliflower mosaic virus (CaMV), and rubber elongation factor (REF) promoter; and promoters for expression using insect cells as hosts, such as polyhedrin promoter and p10 promoter, can be used. These promoters can be selected as appropriate according to the host that expresses the above-mentioned peptides.

The expression vectors mentioned above may further have a multi-cloning site, an enhancer, a splicing signal, a poly(A) addition signal, a selected marker, a replication origin, and the like.

[Carrier]

According to an embodiment, the invention provides a carrier including the peptide described above.

When the carrier of the present embodiment is used, an objective substance can be delivered to pancreatic cancer conveniently and efficiently.

It is preferable that the carrier of the present embodiment further includes a marker or a modifier. Furthermore, the carrier of the present embodiment may also include both a marker and a modifier. The marker or the modifier may be physically or chemically bonded to the above-mentioned peptide directly or via a linker. Specifically, the marker or the modifier may be bonded by coordination bonding, covalent bonding, hydrogen bonding, hydrophobic interaction, or physical adsorption, and any known bonding, linker, and bonding method can be employed. The position of bonding may be any of the N-terminal and the C-terminal of the peptide described above.

Examples of the marker include a stable isotope, a radioisotope, a fluorescent substance, a nuclide for Positron Emission Tomography (PET), a nuclide for Single photon emission computed tomography (SPECT), a Magnetic resonance imaging (MRI) contrast agent, a Computed Tomography (CT) contrast agent, and a magnetic body. Among them, a stable isotope, a radioisotope, or a fluorescent substance is preferred. By including the marker, it can be checked conveniently with high sensitivity whether an objective substance has been delivered to pancreatic cancer cells and tissues.

Examples of the stable isotope include $^{13}$C, $^{15}$N, $^{2}$H, $^{17}$O, and $^{18}$O. Examples of the radioisotope include $^{3}$H, $^{14}$C, $^{13}$N, $^{32}$P, $^{33}$P, and $^{35}$S. In a case in which the marker is a stable isotope or a radioisotope, the above-mentioned peptide may be produced by using stable isotope-labeled amino acids or radioisotope-labeled amino acids. Examples of an amino acid that is labeled with a stable isotope or a radioisotope include 20 kinds of amino acids (alanine, arginine, aspartic acid, glutamic acid, glycine, histidine, isoleucine, leucine, lysine, methionine, phenylalanine, proline, serine, threonine, tyrosine, valine, tryptophan, cysteine, asparagine, and glutamine), and there are no particular limitations as long as the amino acid is an amino acid which is included in the above-mentioned peptide. The amino acid may be an L-form or a D-form, and can be selected as appropriate according to necessity.

The above-mentioned stable isotope-labeled or radioisotope-labeled peptide can be produced by expressing the above-mentioned vector including a nucleic acid that encodes the peptide mentioned above, in a system in which a stable isotope-labeled amino acid or a radioisotope-labeled amino acid exists. An example of the system in which a stable isotope-labeled amino acid or a radioisotope-labeled amino acid exists may be a cell-free peptide synthesis system or a living cell peptide synthesis system, in which a stable isotope-labeled amino acid or a radioisotope-labeled amino acid exists. That is, the aforementioned peptide that is labeled with a stable isotope or labeled with a radioisotope can be produced from the aforementioned vector including a nucleic acid that encodes the aforementioned peptide, by synthesizing a peptide using stable isotope-labeled amino acids or radioisotope-labeled amino acids as well as non-stable isotope-labeled amino acids or non-radioisotope-labeled amino acids as materials in a cell-free peptide synthesis system, or by culturing cells that have been transformed with the aforementioned vector including a nucleic acid that encodes the aforementioned peptide, in the presence of a stable isotope-labeled amino acid or a radioisotope-labeled amino acid in a living cell peptide synthesis system.

The expression of the stable isotope-labeled or radioisotope-labeled, aforementioned peptide using a cell-free peptide synthesis system can be carried out using non-stable isotope-labeled amino acids or non-radioisotope-labeled amino acids needed for the synthesis of the aforementioned peptide that is stable isotope-labeled or radioisotope-labeled, a cell extract for cell-free peptide synthesis, energy sources (high energy phosphate bond-containing substances such as ATP, GTP, and creatine phosphate), and the like, in addition to the aforementioned vector including a nucleic acid that encodes the aforementioned peptide or the stable isotope-labeled amino acid or radioisotope-labeled amino acid. Regarding the reaction conditions such as temperature and time, the reaction can be carried out by selecting the optimal conditions as appropriate, and for example, the temperature is 20° C. to 40° C., and preferably 23° C. to 37° C., while the reaction time is 1 to 24 hours, and preferably 10 to 20 hours.

According to the present specification, the "cell extract for cell-free peptide synthesis" means a liquid extract obtained from plant cells, animal cells, fungal cells, or bacterial cells, which includes components required for a translation system, or a transcription system and a translation system, involved in the synthesis of proteins such as ribosome and tRNA. Specific examples include cell extracts of *Escherichia coli*, wheat germ, rabbit reticulocytes, mouse L-cells, Ehrlich ascites carcinoma cells, HeLa cells, CHO cells, and budding yeast. The production of such a cell extract can be carried out by, for example, disrupting the above-described cells using a French press, glass beads, an ultrasonic disrupting apparatus, or the like, adding a buffer solution containing various kinds of salts for solubilizing protein components or ribosome, homogenizing the mixture, and precipitating insoluble components by centrifugation, according to the method described in Pratt, J. M., et al., Transcription and translation—a practical approach (1984), pp. 179-209.

Furthermore, the expression of the stable isotope-labeled or radioisotope-labeled, aforementioned peptide using a cell-free peptide synthesis system may be carried out by, for example, appropriately using a commercially available kit such as Premium Expression Kit (manufactured by Cellfree Sciences Co., Ltd.) including a wheat germ extract; or RTS 100, *E. coli* HY Kit (manufactured by Roche Applied Science Company), or MUSAIBO-KUN QUICK (manufactured by Taiyo Nippon Sanso Corporation), all including an *Escherichia coli* extract. In a case in which the stable isotope-labeled or radioisotope-labeled peptide thus expressed is insoluble, the peptide may be solubilized as appropriate by using a protein denaturing agent such as guanidine hydrochloride or urea. The stable isotope-labeled or radioisotope-labeled peptide can be further processed by a fractionation treatment such as a fractionation centrifugation method or a sucrose density gradient centrifugation method; or a purification treatment using an affinity column or ion exchange chromatography.

The expression of the stable isotope-labeled or radioisotope-labeled, aforementioned peptide using a living cell peptide synthesis system can be carried out by introducing the aforementioned vector including a nucleic acid that encodes the aforementioned peptide into living cells, and culturing such living cells in a culture fluid including nutrients and antibiotic substances, as well as the stable isotope-labeled amino acid or the radioisotope-labeled amino acid, non-stable isotope-labeled amino acids or non-radioisotope-labeled amino acids needed for the synthesis of a stable isotope-labeled peptide or a radioisotope-labeled peptide, and the like. Here, the living cells are not particularly limited as long as the cells are living cells capable of expressing the aforementioned vector including a nucleic acid that encodes the aforementioned peptide, and examples include mammalian cell lines such as Chinese hamster ovarian (CHO) cells; and living cells such as *Escherichia coli*, yeast cells, insect cells, and plant cells. When considered from the aspects of convenience and cost-effectiveness, *Escherichia coli* is preferred. The expression of the aforementioned vector including a nucleic acid that encodes the aforementioned peptide can be carried out by incorporating the nucleic acid by a gene recombination technology into an expression vector that is designed to be expressed in the respective living cells, and introducing such an expression vector into living cells. Furthermore, introduction of the vector including a nucleic acid that encodes the aforementioned peptide can be carried out by a method appropriate for the living cells used, and examples include an electroporation method, a heat shock method, a calcium phosphate method, a lipofection method, a DEAE dextran method, a microinjection method, a particle gun method, a method using a virus, and methods using commercially available transfection reagents such as FuGENE® 6 Tansfection Reagent (manufactured by Roche Holding AG), Lipofectamine 2000 Reagent (manufactured by Invitrogen, Inc.), Lipofectamine LTX Reagent (manufactured by Invitrogen, Inc.), and Lipofectamine 3000 Reagent (manufactured by Invitrogen, Inc.).

The stable isotope-labeled or radioisotope-labeled, aforementioned peptide that has been expressed by a living cell peptide synthesis system can be processed by subjecting the living cells containing the stable isotope-labeled or radioisotope-labeled peptide to a disruption treatment or an extraction treatment. Examples of the disruption treatment include a freeze-thawing method and physical disrupting treatments using a French press, glass beads, a homogenizer, and an ultrasonic disrupting apparatus. Examples of the extraction treatment include extraction treatments using protein denaturing agents such as guanidine hydrochloride and urea. The stable isotope-labeled or radioisotope-labeled peptide can be further processed by a fractionation treatment such as a fractionation centrifugation method or a sucrose density gradient centrifugation method; a purification treatment using an affinity column or ion exchange chromatography; or the like.

Examples of the fluorescent substance include known quantum dots, Indocyanine Green, 5-aminolevulinic acid (5-ALA; metabolite protoporphyrin IX (PP IX), near-infrared fluorescent dyes (for example, Cy5.5, Cy7, and AlexaFluoro), and other known fluorescent dyes (for example, GFP, Fluorescein (FITC), and TAMRA). The aforementioned peptide that is labeled with a fluorescent substance may be produced by incorporating a fluorescent substance and the aforementioned vector including a nucleic acid that encodes the aforementioned peptide into the above-described cell-free peptide synthesis system or living cell peptide synthesis system, without using a stable isotope-labeled amino acid or a radioisotope-labeled amino acid.

Preferred examples of the nuclide for PET and the nuclide for SPECT include $^{11}$C, $^{13}$N, $^{15}$O, $^{18}$F, $^{66}$Ga, $^{67}$Ga, $^{68}$Ga, $^{60}$Cu, $^{61}$Cu, $^{62}$Cu, $^{67}$Cu, $^{64}$Cu, $^{48}$V, Tc-99m, $^{241}$Am, $^{55}$Co, $^{57}$Co, $^{153}$Gd, $^{111}$In, $^{133}$Ba, $^{82}$Rb, $^{139}$Ce, Te-123m, $^{137}$Cs, $^{86}$Y, $^{90}$Y, $^{185/187}$Re, $^{186/188}$Re, $^{125}$I, and complexes thereof, or combinations thereof. The aforementioned peptide that is labeled with a nuclide for PET or a nuclide for SPECT may be produced by incorporating the aforementioned vector including a nucleic acid that encodes the aforementioned peptide into the cell-free peptide synthesis system or living cell peptide synthesis system described above.

Examples of the MRI contrast agent, CT contrast agent, and magnetic body include gadolinium, Gd-DTPA, Gd-DTPA-BMA, Gd-HP-DO3A, iodine, iron, iron oxide, chromium, manganese, and complexes thereof or chelate complexes thereof. The aforementioned peptide that is labeled with an MRI contrast agent, a CT contrast agent or a magnetic body may be produced by physically or chemically bonding the MRI contrast agent, CT contrast agent or magnetic body to the aforementioned peptide directly or via a linker. Specific examples of the bonding include coordination bonding, covalent bonding, hydrogen bonding, hydrophobic interaction, and physical adsorption, and any known bonding, linker, and bonding method can be employed.

Examples of the modifier include a sugar chain and polyethylene glycol (PEG). By including the modifier described above, an objective substance becomes likely to be absorbed into pancreatic cancer cells conveniently and efficiently. The aforementioned peptide that is modified with a modifier may be produced by physically or chemically bonding the modifier to the aforementioned peptide directly or via a linker. Specific examples of the bonding include coordination bonding, covalent bonding, hydrogen bonding, hydrophobic interaction, and physical adsorption, and any known bonding, linker, and bonding method can be employed. The position of bonding may be any of the N-terminal and the C-terminal of the aforementioned peptide.

In regard to the carrier of the present embodiment, the objective substance can be selected as appropriate according to the use, and for example, in a case in which the carrier is used for imaging of pancreatic cancer, as will be described below, the marker described above can be included as an objective substance, and in a case in which the carrier is used for the use in the treatment or diagnosis of pancreatic cancer, as will be described below, a physiologically active substance can be included as an objective substance. The objective substance may be physically or chemically bonded to the aforementioned peptide directly or via a linker. Specific examples of the bonding include coordination bonding, covalent bonding, hydrogen bonding, hydrophobic interaction, and physical adsorption, and any known bonding, linker, and bonding method can be employed. Furthermore, the position of bonding between the objective substance and the carrier can be selected as appropriate according to necessity.

In regard to the carrier of the present embodiment, in a case in which the objective substance is a protein, a fusion protein including the objective substance and the aforementioned peptide can be produced by, for example, the following method. First, a host is transformed using an expression vector including a nucleic acid that encodes a fusion protein. Subsequently, the host is cultured, and the fusion protein is expressed. The conditions such as the composition of the culture medium, the temperature and time of culture, and the addition of an inducer, can be determined by a person having ordinary skill in the art according to a known method, so that the transformant grows and the fusion protein is produced efficiently. Furthermore, for example, in a case in which an antibiotic substance-resistant gene is incorporated as a selected marker into the expression vector, the transformant can be selected by adding an antibiotic substance to the medium. Subsequently, the fusion protein expressed by the host is purified by an appropriate method, and thereby the fusion protein is obtained.

The host is not particularly limited as long as the host is a living cell capable of expressing an expression vector including a nucleic acid that encodes the fusion protein, and examples include living cells, such as mammalian cell lines such as Chinese hamster ovarian (CHO) cells; microorganisms such as viruses (for example, viruses such as adenovirus, adeno-associated virus, lentivirus, vaccinia virus, baculovirus, retrovirus, and hepatitis virus), and bacteria (for example, *Escherichia coli*); yeast cells, insect cells, and plant cells.

Furthermore, in regard to the carrier of the present embodiment, an expression vector including a nucleic acid that encodes the above-described fusion protein may also be introduced directly into pancreatic cancer cells or tissues and expressed therein.

[Pharmaceutical Composition]

According to an embodiment, the invention provides a pharmaceutical composition including the aforementioned carrier and a physiologically active substance.

When the pharmaceutical composition of the present embodiment is used, pancreatic cancer (particularly, invasive pancreatic duct cancer) can be selectively treated.

According to the present specification, the "physiologically active substance" is not particularly limited as long as it is effective for the treatment of pancreatic cancer, and examples include a drug such as an anticancer drug, a nucleic acid, an antibody that binds specifically to pancreatic cancer, an antibody fragment, and an aptamer.

The "physiologically active substance" is preferably a molecular target drug having pancreatic cancer-selective cytotoxic activity; however, since the physiologically active substance is pancreatic cancer-selectively accumulated by the aforementioned carrier, the physiologically active substance may also be a cytotoxic drug that is being used as a conventional anticancer agent.

The physiologically active substance may be physically or chemically bonded to the aforementioned carrier directly or via a linker. Specific examples of the bonding include coordination bonding, covalent bonding, hydrogen bonding, hydrophobic interaction, and physical adsorption, and any known bonding, linker, and bonding method can be employed. Furthermore, the position of bonding between the physiologically active substance and the aforementioned carrier can be selected as appropriate according to necessity. In regard to the pharmaceutical composition of the present embodiment, the aforementioned carrier may include the aforementioned marker or modifier.

Examples of the nucleic acid include siRNA, miRNA, an antisense, and an artificial nucleic acid compensating the functions of those materials.

The antibody can be produced by, for example, immunizing a rodent animal such as a mouse with a pancreatic cancer-derived peptide or the like as an antigen. Furthermore, for example, the antibody can be produced by screening of a phage library. Examples of the antibody fragment include Fv, Fab, and scFv.

An aptamer is a substance having a specific binding capacity for pancreatic cancer. Examples of the aptamer include a nucleic acid aptamer and a peptide aptamer. A nucleic acid aptamer having a specific binding capacity for pancreatic cancer can be screened by, for example, a systematic evolution of ligand by exponential enrichment (SELEX) method. A peptide aptamer having a specific binding capacity for pancreatic cancer can be screened by, for example, a Two-hybrid method using yeast.

The pharmaceutical composition of the present embodiment can be used for the diagnosis of pancreatic cancer, diagnosis of the effect of pancreatic cancer treatment, a pathological analysis, treatment of pancreatic cancer, or the diagnosis, pathological analysis, treatment, and diagnosis of the effect of treatment of a disease associated with pancreatic cancer. Examples of a diagnosis method of using the pharmaceutical composition of the present embodiment include PET, SPECT, CT, MRI, diagnosis by endoscopy, and diagnosis by means of a fluorescence detector.

<Amount of Administration>

The pharmaceutical composition of the present embodiment is regulated as appropriate in consideration of the age, gender, body weight, and symptoms of a test animal (various mammals including a human being or non-human animals, and preferably a human being), the therapeutic method, the administration method, the treatment time, and the like.

For example, in the case of intravenously (i.v.) injecting the pharmaceutical composition of the present embodiment by means of an injectable preparation, it is preferable that the pharmaceutical composition is administered in an amount of 5 mg or more in terms of the peptide per kilogram of the body of the test animal (preferably, a human being) in a single administration; it is more preferable that the pharmaceutical composition is administered in an amount of from 5 mg to 15 mg in terms of the peptide; and it is particularly preferable that the pharmaceutical composition is administered in an amount of from 5 mg to 10 mg in terms of the peptide.

Regarding the number of times of administration, it is preferable that the pharmaceutical composition is administered once to several times per week on the average.

Examples of the dosage form include methods known to those ordinarily skilled in the art, such as intraarterial injection, intravenous injection, subcutaneous injection, and intranasal, intraperitoneal, transbronchial, intramuscular, percutaneous, or peroral administration, and intravenous injection or intraperitoneal administration is preferred.

<Composition Components>

The pharmaceutical composition of the present embodiment includes therapeutically effective amounts of the aforementioned carrier and physiologically active substance, and a pharmaceutically acceptable carrier or diluent. Examples of the pharmaceutically acceptable carrier or diluent include an excipient, a diluent, an extending agent, a disintegrant, a stabilizer, a preservative, a buffering agent, an emulsifier, a flavoring agent, a colorant, a sweetener, a thickening agent, a corrigent, a dissolution aid, and additives. By using one or more of these carriers, a pharmaceutical composition in the form of an injectable preparation, a liquid preparation, a capsule, a suspension, an emulsion, or a syrup can be prepared.

Furthermore, a colloidal dispersion system can also be used as the carrier. A colloidal dispersion system is expected to have an effect of increasing in vivo stability of the peptide or an effect of increasing the migrating properties of the peptide to a particular organ, tissue, or cells. Examples of the colloidal dispersion system include polyethylene glycol, a polymer composite, a polymer aggregate, nanocapsules, microspheres, beads, an emulsifier for an oil-in-water system, and lipids including micelles, mixed micelles, and liposomes. Liposomes or vesicles of artificial membranes, which have an effect of efficiently transporting the peptide to a particular organ, tissue, or cells, are preferred.

Examples of the formulation for the pharmaceutical composition of the present embodiment include those formulations orally used as a tablet that is optionally provided with a sugar coating, a capsule preparation, an elixir preparation, or a microcapsule preparation.

Alternatively, a pharmaceutical composition that is parenterally used in the form of an injectable preparation of an aseptic solution or a liquid suspension with water or other pharmaceutically acceptable liquids, may be mentioned. A pharmaceutical composition that has been formulated by appropriately combining a pharmacologically acceptable carrier or diluent, specifically, sterilized water, physiological saline, a plant oil, an emulsifier, a suspending agent, a surfactant, a stabilizer, a flavoring agent, an excipient, a vehicle, an antiseptic agent, a binder, and the like, and mixing the mixture into a unit dosage form required for generally acknowledged medicine manufacture procedure, may be mentioned.

Examples of the additives that can be mixed in tablets and capsules include binders such as gelatin, corn starch, tragacanth gum, and gum Arabic; excipients such as crystalline cellulose; swelling agents such as corn starch, gelatin, and alginic acid; lubricating agents such as magnesium stearate; sweetening agents such as sucrose, lactose, and saccharin; and flavoring agents such as peppermint, akamono oil, and cherry flavor. In a case in which the preparation unit dosage form is a capsule, a liquid carrier such as fats and oils can be further incorporated into the materials described above.

An aseptic composition for injection can be prescribed according to the conventional formulation procedure, using a vehicle such as distilled water for injection.

Examples of an aqueous solution for injection include physiological saline, and an isotonic liquid including glucose or other auxiliary drugs, for example, D-sorbitol, D-mannose, D-mannitol, and sodium chloride. This may also be used in combination with an appropriate dissolution aid, for example, an alcohol, specifically, ethanol; polyalcohol, for example, propylene glycol, polyethylene glycol; a nonionic surfactant, for example, Polysorbate 80™, and HCO-50.

Examples of an oily liquid for injection include sesame oil and soybean oil, and the oily liquid may be used in combination with benzyl benzoate or benzyl alcohol as a dissolution aid. Furthermore, a buffering agent (for example, a phosphate buffer solution or a sodium acetate buffer solution), a soothing agent (for example, procaine hydrochloride), a stabilizer (for example, benzyl alcohol or phenol), an oxidation inhibitor, and the like may be incorporated. The injection liquid thus prepared is usually charged into an appropriate ampoule.

In the case of an injectable preparation, the injectable preparation may also be prepared as an aqueous or non-aqueous dilution, suspension, or emulsion such as described above. Sterilization of such an injectable preparation can be carried out by filter sterilization using a filter, or incorporation of a disinfectant or the like. An injectable preparation can be produced in the form of prior preparation. That is, an aseptic solid composition is produced by a freeze-drying method, the solid composition is dissolved in distilled water for injection or another solvent before use, and thus the solution can be used.

<Therapeutic Method>

According to an aspect of the invention, there is provided a pharmaceutical composition including the aforementioned carrier for the treatment of pancreatic cancer, and a physiologically active substance.

According to an aspect of the invention, there is provided a pharmaceutical composition including therapeutically effective amounts of the aforementioned carrier and a physiologically active substance, and a pharmaceutically acceptable carrier or diluent.

According to an aspect of the invention, there is provided a therapeutic agent for pancreatic cancer, including the pharmaceutical composition.

According to an aspect of the invention, there is provided a use of the aforementioned carrier and a physiologically active substance for producing a therapeutic agent for pancreatic cancer.

According to an aspect of the invention, there is provided a method for treating pancreatic cancer, the method including administering effective amounts of the aforementioned carrier and a physiologically active substance to a patient in need of treatment.

[Method for Imaging Pancreatic Cancer]

According to an embodiment, the invention provides a method for imaging pancreatic cancer, the method including using the aforementioned carrier.

According to the method of the present embodiment, pancreatic cancer can be conveniently and selectively detected with high sensitivity.

In regard to the method of the present embodiment, it is preferable that the aforementioned carrier includes a marker. The carrier may further include a modifier. Examples of the marker and the modifier include compounds similar to those mentioned above.

For example, in a case in which the aforementioned carrier including a marker is added to pancreatic cancer cells, the amount of addition of the aforementioned carrier including a marker is preferably from 1 μM to 4 μM in the culture fluid. Furthermore, after the addition, after a period of from 30 minutes to 3 hours, an evaluation can be carried out on whether the carrier has accumulated in pancreatic cancer cells.

For example, in a case in which the aforementioned carrier including a fluorescent substance as a marker is intravenously (i.v.) injected using an injectable preparation, for a test animal (preferably, a human being), it is preferable to administer an amount of 5 mg or more in terms of the peptide per kilogram of the body weight in a single administration, it is more preferable to administer an amount of from 5 mg to 15 mg in terms of the peptide, and it is particularly preferable to administer an amount of from 5 mg to 10 mg in terms of the peptide.

Furthermore, for example, in the case of intravenously (i.v.) injecting the aforementioned carrier including a stable isotope, a nuclide for PET, or a nuclide for SPECT as a marker using an injectable preparation, the amount of administration may be determined from the dose of radiation according to the stable isotope, the nuclide for PET, or the nuclide for SPECT used.

In regard to the method of the present embodiment, examples of a method for detecting the aforementioned carrier including a marker include PET, SPECT, CT, MRI, detection by endoscopy, and detection using a fluorescence detector.

EXAMPLES

Hereinafter, the present invention will be explained by way of Examples; however, the invention is not intended to be limited to the following Examples.

[Example 1] Synthesis of Peptide

The various peptides (Peptide 1 to Peptide 4) shown in the following Table 1 were separated and identified according to a known IVV (in vitro virus) method, using an autonomously produced protein-RNA chimera type random peptide library (in vitro virus library; IVVL) having a 9-amino acid residue peptide or 15-amino acid residue peptide as the phenotype and a mRNA coding sequence as the genotype corresponding thereto, with puromycin being interposed therebetween. Furthermore, the various IVVL-derived peptides thus identified were synthesized under Fluorescein isothiocyanate (FITC) labeling, and the peptides were subjected to a hydrochloride treatment. Furthermore, r9 (D-ar-ginine for nine successive residues) is a non-selective membrane-permeable peptide that is currently widely used.

These were all obtained by consignment synthesis provided by Sigma-Aldrich Japan K.K. (Genosys Division).

TABLE 1

| Name | Amino acid sequence (one-letter code) | SEQ ID NO. |
|---|---|---|
| Peptide 1 | GYRRTTPSYWRMWLR | 1 |
| Peptide 2 | ARRYTWIRA | 2 |
| Peptide 3 | RAWRQCRWR | 3 |
| Peptide 4 | RRPTTWHKP | 4 |
| r9 | RRRRRRRRR | 13 |

The cell lines and the origins of the various cells used in the following Test Examples 1 and 2 were as shown in the following Table 2. These were maintained by subculture in the laboratory by the inventors.

TABLE 2

| Type of cells | Cell line | Origin |
|---|---|---|
| Pancreatic cancer cells | BxPC3 | Human pancreatic cancer cell line |
| | PK-8 | Human pancreatic cancer cell line |
| | PL45 | Human pancreatic cancer cell line (low differentiation type) |
| | AsPC1 | Human pancreatic cancer cell line (low differentiation type) |
| | Panc1 | Human pancreatic cancer cell line |
| Other cancer cells | KYN-2 | Human hepatocellular carcinoma cell line |
| Normal cells | HaCaT | Human immortalized normal keratinocyte cell line |
| | Kidney | Human immortalized normal renal epithelial cell line |
| | NHDF | Human normal dermal fibroblast cell line |
| | NuLi-1 | Human immortalized normal bronchial epithelial cell line |
| | HPNE | Human immortalized normal pancreatic duct epithelial cell line |
| | MMNK-1 | Human immortalized normal bile duct epithelial cell line |
| | Liver | Human normal liver cell line |
| | TIME | Human immortalized vascular endothelial cell line |

Pancreatic cancer cells and HPNE cells were cultured using a 5% FBS-containing CS-C medium kit. KYN-2 cells, HaCaT cells, NHDF cells, MMNK-1 cells, and Liver cells were cultured using 10% FBS-containing RPMI1640 medium. Kidney cells were cultured using a proliferation medium for normal human renal epithelial cells (RenaLife Comp Kit). NuLi-1 cells were cultured using BEGM medium (Bronchial Epithelial Growth Medium, Serum-free). TIME cells were cultured using EBM-2-MV Bullet kit (Endothelial Cell Basal Medium-2 Bullet kit).

[Test Example 1] Test for Confirmation of Accumulation of Peptide to Pancreatic Cancer Cells, Other Cancer Cells, and Normal Cells Originating From Various Tissues To the various pancreatic cancer cells, KYN-2 cells, and normal cells originating from various tissues as indicated in Table 2, Peptide 1, Peptide 2, Peptide 3, and Peptide 4 produced in Example 1, and r9 peptide were respectively added to the culture medium so as to obtain a final concentration of 2 µM. Those cells were cultured for 2 hours at 37° C. Subsequently, the cells were washed three times with the medium in order to remove the peptide-containing medium. Subsequently, the uptake of the various peptides in the living cells was visually evaluated using an inverted type fluorescence microscope. Prior to the microscopic examination, the culture supernatant containing the peptides were removed, the cells were washed three times with 1×PBS (−), and then the cells were treated with trypsin. Adherent cells were detached and were immediately transferred into a fresh 96-well plate. The cells were resuspended in a fresh culture fluid, and then a microscopic examination was performed. The results are shown in FIG. 1.

From FIG. 1, in regard to Peptide 1, Peptide 2, Peptide 3, and Peptide 4, it became clear that fluorescence was hardly detected in KYN-2 cells and normal cells originating from various tissues, and strong fluorescence was detected in the various pancreatic cancer cells.

Figure 2A:
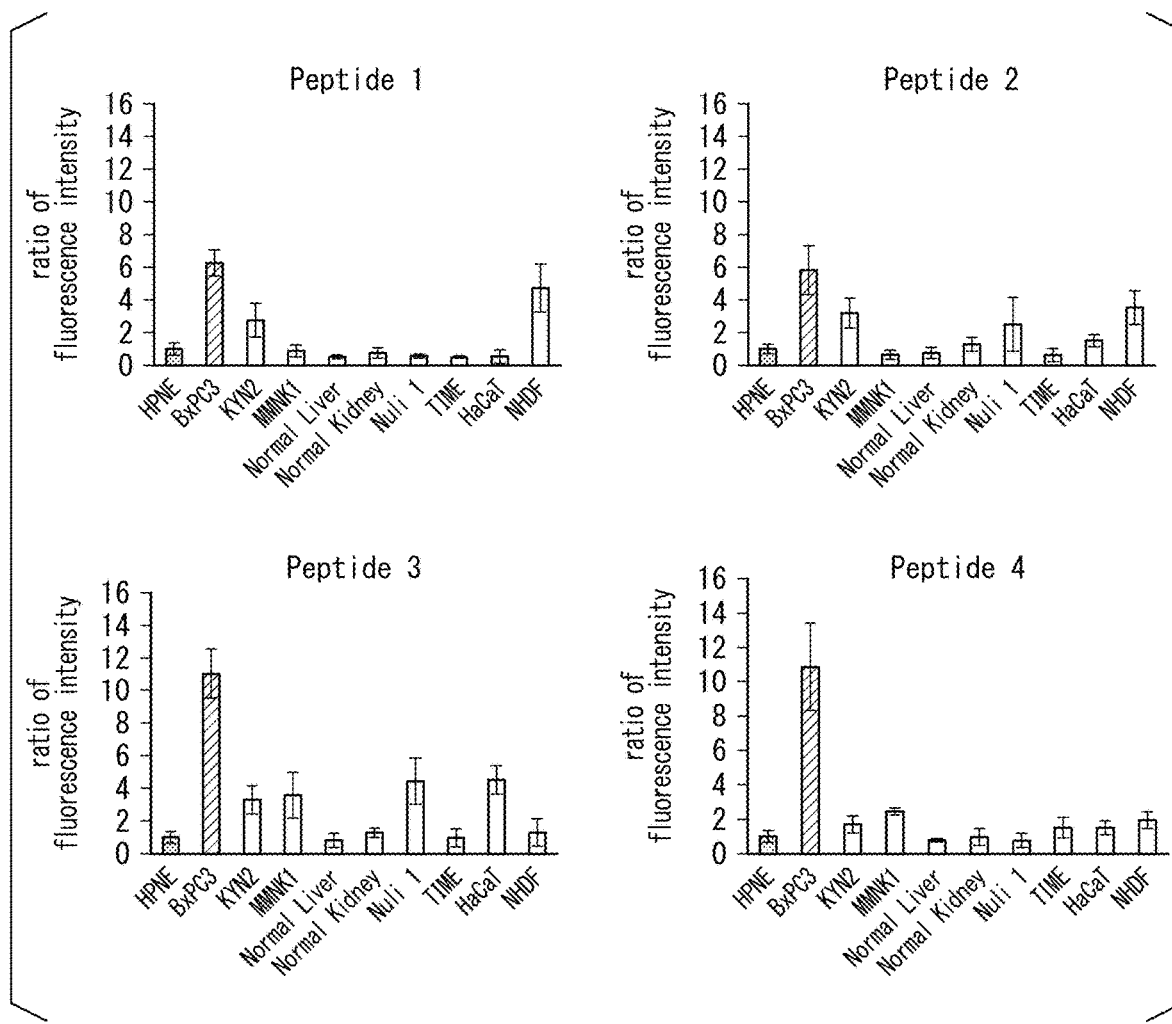
FIG. 2A is a graph showing the proportions of the fluorescence intensities detected in various cells, the proportions being obtained by quantitatively analyzing the fluorescence detected in the various cells to which various peptides were added in Test Example 1, and determining relative values by designating the fluorescence detected in HPNE cells, which are a human immortalized normal pancreatic duct epithelial cell line, as 1.0.

The graph of FIG. 2A is a graph showing the proportions of fluorescence intensities detected in various cells, the proportions being obtained by quantitatively analyzing the fluorescence detected in the various cells to which various peptides were added in Test Example 1, and determining relative values by designating the fluorescence detected in HPNE cells, which are a human immortalized normal pancreatic duct epithelial cell line, as 1.0.

From FIG. 2A, it was confirmed that in BxPC3 cells to which Peptide 1 to Peptide 4 were added, stronger fluorescence was detected compared to the other cells.

Figure 2B:
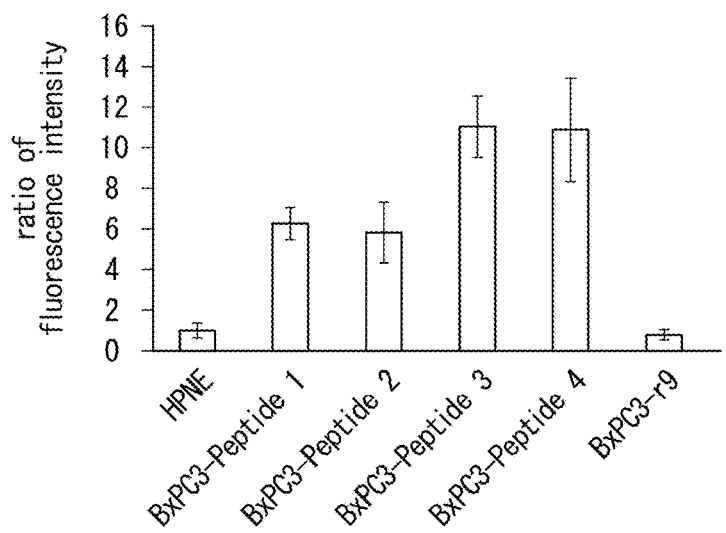
FIG. 2B is a graph showing the proportions of the fluorescence intensity detected in BxPC3 cells to which various peptides were added in Test Example 1, the fluorescence intensities being relative values determined by designating the fluorescence detected in HPNE cells, which are a human immortalized normal pancreatic duct epithelial cell line, as 1.0.

FIG. 2B is a graph showing the proportions of the fluorescence intensity detected in BxPC3 cells to which various peptides were added in Test Example 1, the fluorescence intensities being relative values determined by designating the fluorescence detected in HPNE cells, which are a human immortalized normal pancreatic duct epithelial cell line, as 1.0.

From FIG. 2B, in regard to Peptide 1 and Peptide 2, when the absorption into normal pancreatic duct epithelial cells was designated as 1.0, the absorption ratio (S/N ratio: Signal/noise ratio) into BxPC3 cells, which were target pancreatic cancer cells, was about 6 times. Furthermore, in regard to Peptide 3 and Peptide 4, strong fluorescence signals were detected in BxPC3 cells, which were target pancreatic cancer cells, with a S/N ratio of 10 times or greater.

Figure 3A:
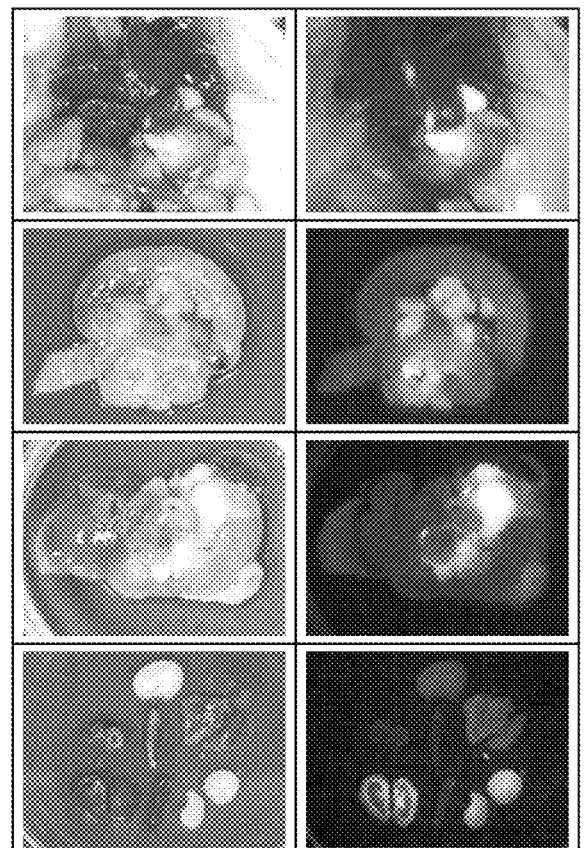
FIG. 3A is a set of fluorescence microscopic photographs of the bright field and the dark field of various tissues of a mouse that was transplanted with Panc1 cells, which are human pancreatic cancer cells, into the abdominal cavity and intravenously injected with Peptide 1 in Test Example 2.
Figure 3B:
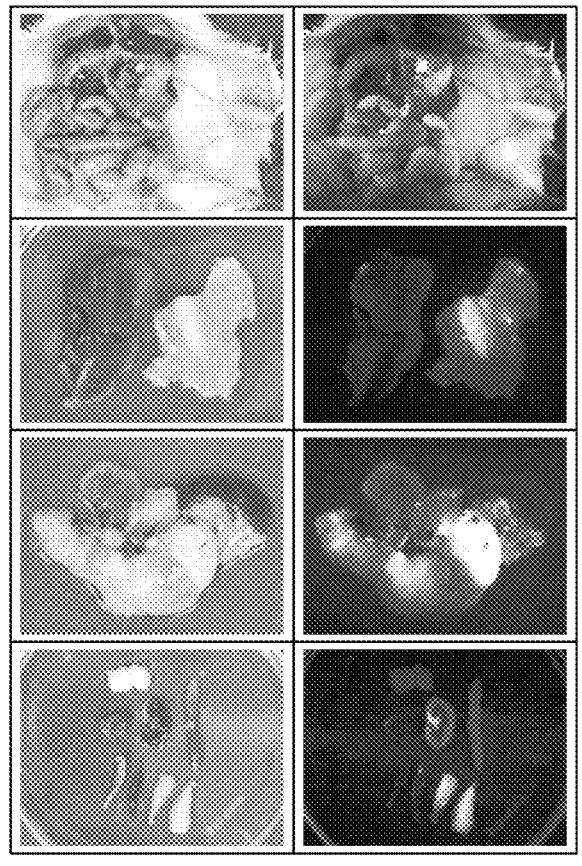
FIG. 3B is a set of fluorescence microscopic photographs of the bright field and the dark field of various tissues of a mouse that was transplanted with PK-8 cells, which are human pancreatic cancer cells, into the abdominal cavity and intravenously injected with Peptide 1 in Test Example 2.

[Test Example 2] Test for Evaluation of Accumulation of Peptide in Various Tissues in Human Pancreatic Cancer Cell-Transplanted Mouse NOD-SCID mice (six-week-old female mice purchased from Crea-Japan, Inc.) intraperitoneally transplanted with Panc1 cells or PK-8 cells, which are human pancreatic cancer cells, in an amount of 1×10$^6$ cells in each animal, were produced as human pancreatic cancer cell-transplanted mice. Thirty days after the transplantation of human pancreatic cancer cells, Peptide 1 produced in Example 1 was intravenously (i.v.) injected to the mice in an amount of 300 µg with respect to 20 g of the mouse body weight. The mice were subjected to laparotomy 30 minutes after the administration, and in a freshly extracted state, the distribution of the peptide and the fluorescence intensities in the tumor lesions and the normal organ groups were observed with a fluorescence stereoscopic microscope. The results are presented in FIG. 3A and FIG. 3B. In FIG. 3A and FIG. 3B, the "Bright Field" refers to images taken in the bright field, and "FITC" refers to images taken in the dark field under the conditions of green fluorescence excitation at a wavelength of 488 nm.

In FIG. 3A and FIG. 3B, strong fluorescence of FITC was detected in the tumor and the metastatic lesions. From this, it was confirmed that Peptide 1 has highly-shifted accumulation to pancreatic cancer tissues.

Figure 4:
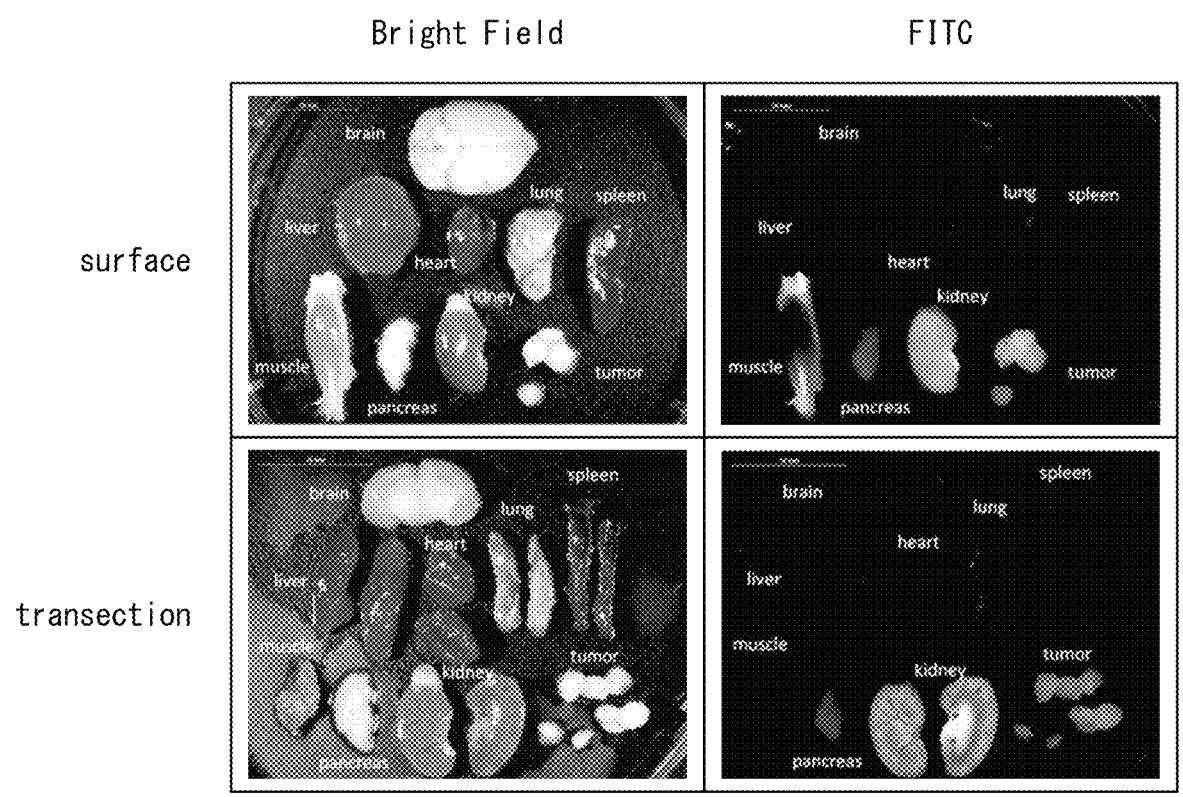
FIG. 4 is a set of fluorescence microscopic photographs of the bright field and the dark field of various tissues of a mouse that was transplanted with BxPC3 cells, which are human pancreatic cancer cells, into the pancreas and intravenously injected with Peptide 4 in Test Example 3.

[Test Example 3] Test for Evaluation of Accumulation of Peptide in Various Tissues in Human Pancreatic Cancer Cell-Transplanted Mouse NOD-SCID mice (six-week-old female mice purchased from Crea-Japan, Inc.) having BxPC3 cells, which are human pancreatic cancer cells, transplanted into the pancreas in an amount of 1×10$^6$ cells in each animal, were produced as human pancreatic cancer cell-transplanted mice. Thirty days after the transplantation of human pancreatic cancer cells, Peptide 4 produced in Example 1 was intravenously (i.v.) injected to the mice in an amount of 150 µg with respect to 20 g of the mouse body weight. The mice were subjected to laparotomy 30 minutes after the administration, and in a freshly extracted state, the distribution of the peptide and the fluorescence intensities in the tumor lesions and the normal organ groups were observed with a fluorescence stereoscopic microscope. The results are presented in FIG. 4. In FIG. 4, the "Bright Field" refers to images taken in the bright field, and "FITC" refers to images taken in the dark field under the conditions of green fluorescence excitation at a wavelength of 488 nm. Furthermore, in FIG. 4, "brain" means the brain, "heart" means the heart, "kidney" means the kidney, "liver" means the liver, "lung" means the lung, "muscle" means the skeletal muscle, "pancreas" means the pancreas, "spleen" means the spleen, and "tumor" means a malignant tumor. "Surface" means the surface of various organs, and "transection" means a transverse section of various organs.

In FIG. 4, strong fluorescence of FITC was detected in the tumor and the kidneys.

Figure 5:
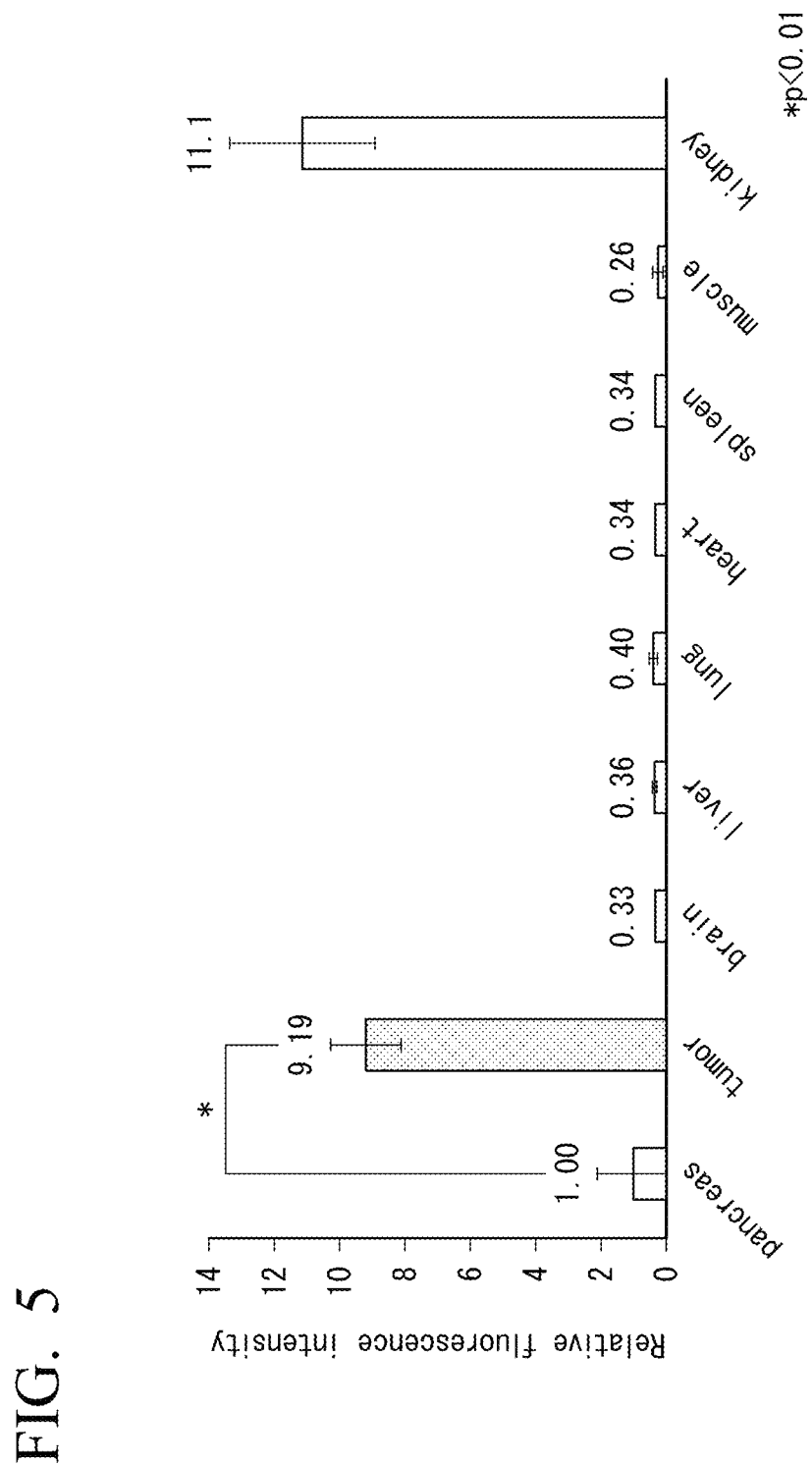
FIG. 5 is a graph showing the proportions of the fluorescence intensities detected in various tissues, the proportions being obtained by quantitatively analyzing the fluorescence detected in a mouse that was intravenously injected with Peptide 3 Peptide 4 in Test Example 3 and determining relative values by designating the fluorescence detected in normal pancreas as 1.0.

FIG. 5 is a graph showing the proportions of the fluorescence intensities detected in various tissues, the proportions being obtained by designating the fluorescence detected in normal pancreas as 1.0.

From FIG. 5, Peptide 4 was such that when the absorption into the normal pancreas was designated as 1.0, the S/N ratio in the target malignant tumor (human pancreatic cancer cells) was about 9 times. Furthermore, in the kidneys, the S/N ratio was about 11 times; however, this was not because Peptide 4 was absorbed into the cells of the kidneys and accumulated therein, but because a portion of intravenously injected Peptide 4 was migrating from the renal vein to the ureter as a urination route to the outside of the body as the diuretic action. Furthermore, the fluorescence at the two terminal parts of the skeletal muscle in the image taken from the surface was caused by autofluorescence exhibited by the tendons attached thereto, and the fluorescence disappeared at a transverse section of the skeletal muscle.

From the above results, it was confirmed that Peptide 4 has highly-shifted accumulation to pancreatic cancer tissues in vivo.

INDUSTRIAL APPLICABILITY

According to the invention, a novel peptide having highly-shifted accumulation to pancreatic cancer cells and tissues can be provided.

Furthermore, pancreatic cancer lesions including metastatic lesions can be conveniently and selectively detected in vivo with high sensitivity.

What is claimed is:

1. A peptide consisting of:
   (a) the amino acid sequence of SEQ ID NO: 4; or
   (b) an amino acid sequence having at least 90% identity with the amino acid sequence of SEQ ID NO: 4.

2. The peptide according to claim 1, wherein the peptide comprises L-amino acids.

3. A carrier comprising a peptide of claim 1; and a marker or modifier, bonded to the peptide.

4. The carrier according to claim 3, wherein the marker is one selected from the group consisting of a stable isotope, a radioisotope, and a fluorescent substance.

5. The carrier according to claim 3, wherein the modifier is one selected from the group consisting of a sugar chain and polyethylene glycol.

6. A pharmaceutical composition comprising:
   a peptide of claim 1; and
   a physiologically active substance.

* * * * *